United States Patent [19]

Uda et al.

[11] Patent Number: 4,670,419

[45] Date of Patent: Jun. 2, 1987

[54] PHARMACEUTICAL COMPOSITION AND ITS RECTAL USE

[75] Inventors: Yoshiaki Uda, Takarazuka; Shin-ichiro Hirai, Kyoto; Takatsuka Yashiki, Takarazuka, all of Japan

[73] Assignee: Takeda Chemical Industries, Ltd., Osaka, Japan

[21] Appl. No.: 753,816

[22] Filed: Jul. 8, 1985

Related U.S. Application Data

[63] Continuation of Ser. No. 487,831, Apr. 22, 1983, abandoned.

[30] Foreign Application Priority Data

Jul. 28, 1982 [JP] Japan ................................ 57-132658

[51] Int. Cl.$^4$ ...................... A61K 37/24; A61K 37/43
[52] U.S. Cl. ........................................ 514/16; 514/17; 514/18; 514/19; 514/800; 514/806; 514/807; 514/809

[58] Field of Search ................... 514/17, 18, 16, 19, 514/806, 807, 809

[56] References Cited

FOREIGN PATENT DOCUMENTS

2090738 .7/1982 United Kingdom .

OTHER PUBLICATIONS

Yakugaku Zasshi 97 (7), 705–711 (1977).
Yakugaku Zasshi 101 (10), 857–873 (1981).
Arzneimittel-Forschung, 1973, pp. 424–426.
Chemical & Pharmaceutical Bulletin, vol. 30, 1416–1421 (1982).

*Primary Examiner*—Delbert R. Phillips
*Attorney, Agent, or Firm*—Wenderoth, Lind & Ponack

[57] ABSTRACT

A pharmaceutical composition containing a hydrophilic drug which is poorly absorbable through the gastrointestinal tract, and cyclodextrin, increases the absorbability of the drug into the mammalian body when administered by a non-oral or non-injection route.

6 Claims, No Drawings

PHARMACEUTICAL COMPOSITION AND ITS RECTAL USE

This application is a continuation, of now abandoned application Ser. No. 487,831, filed Apr. 22, 1983, now abandoned.

The present invention relates to a pharmaceutical composition and its use.

It is generally known that any highly hydrophilic drug having a small oil/water partition coefficient is hardly absorbed through the gastrointestinal tract and consequently the bioavailability of such drug is small. Therefore, in order to achieve a sufficient clinical effect, such a hydrophilic drug is administered in the form of an injection. However, the administration of a drug by way of injection requires an expert hand and causes pain in the recipient and, for these reasons, it is desired to develop a dosage form other than the injection but capable of being applied in an easy and simple manner and affording a high level of bioavailability.

Under these circumstances, the present inventors conducted an intensive study to develop a preparation form for non-oral and non-injection administration that would be conducive to an improved bioavailability, hence an improved pharmacological effect, of a hydrophilic or water-soluble drug which is poorly absorbable through the gastrointestinal tract. As a result, the present inventors found that when such a drug is used by non-oral and non-injection administration in combination with cyclodextrin, the absorption of the drug is markedly increased. This finding and subsequent research have resulted in the development of the present invention.

The present invention realtes to (1) a pharmaceutical composition which contains a hydrophilic drug, which is poorly absorbable through the gastrointestinal tract, and cyclodextrin and (2) a method of administering a pharmaceutical composition, which contains a hydrophilic drug, which is poorly absorbable through the gastrointestinal tract, and cyclodextrin, from the nasal cavity, the vagina or rectum.

The present pharmaceutical composition contains a hydrophilic drug which is poorly absorbable through the gastrointestinal tract.

The drug which is poorly absorbable through the gastrointestinal tract is a drug the bioavailability of which is preferably not more than about 70 percent, more preferably not more than about 50 percent, and most preferably not more than about 20 percent, for example in experimental animals (rat, dog, rabbit etc.), preferably in humans.

In another aspect, the hydrophilic drug to be used according to this invention is a drug having a small oil/water partition coefficient and more particularly an n-octanol/water partition coefficient of not more than about 10, preferably not more than about 1, more preferably not more than about 0.1.

The oil/water partition coefficient can be determined by the method described in Robert E. Notari "Biopharmaceutics and Pharmacokinetics", Marcel Dekker Inc., 1975, New York, U.S.A. Thus, equal amounts of n-octanol and a buffer solution (pH 5.5) are placed in a test tube to give a 1:1 mixture. The buffer solution is exemplified by Sörensen buffer [Ergebniss der Physiology 12, 393 (1912)], Clark-Lubs buffer [Journal or Bacteriology 2, (1), 109, 191 (1971)], MacIlvaine buffer [Journal Biological Chemistry 49, 183 (1921)], Michaelis buffer [Die Wasser-Stoffionenkonzentration, p. 186 (1914)], Kolthoff buffer [Biochemische Zeitschrift 179, 410 (1926)] and so on. An adequate amount of the drug to be tested is added to the mixture, and the test tube is stoppered, immersed in a constant-temperature bath (25° C.) and shaken vigorously. When it appears that the drug has been dissolved in between the liquid layers and an equilibrium has been reached, the mixture is allowed to stand or is centrifuged, and aliquots of the upper and lower liquid layers are pipetted separately and analyzed for the concentration of the drug in each layer. The ratio of the concentration of the drug in the n-octanol layer to the concentration of the drug in the aqueous layer is the oil/water partition coefficient.

As the drug employed in the present invention, there may be mentioned, for example, physiologically active polypeptides, polysaccharides, aminoglycoside antibiotics, beta-lactam antibiotics, and nucleic acid drugs.

The polypeptides are exemplified by peptides which comprise two or more than two amino acid residues. The polypeptides preferably have a molecular weight of about 200 to 60000.

As the physiologically active polypeptide, there may be mentioned, for example, L-pyroglutamyl-L-histidyl-L-prolinamide (thyrotropin releasing hormone; hereinafter referred to briefly as TRH) or its salts, especially its tartrate [U.S. Pat. No. 3,957,247], and a polypeptide represented by the formula (I)

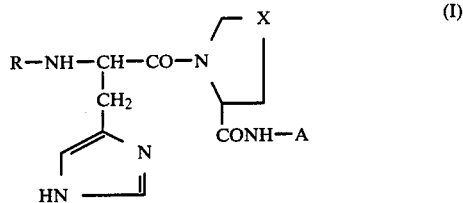

wherein A stands for hydrogen, alkyl, aralkyl, alkoxyalkyl, hydroxyalkyl or alkoxy, R stands for

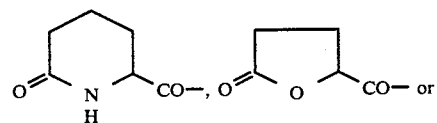

X stands for —CH₂—, —CH₂CH₂— or —S—, R and each of the other constituent amino acid residues may have an L- or D-configuration or be racemic] and salts thereof [U.S. Pat. No. 4,100,152].

Among the compounds represented by the formula (I), the compound shown below is referred to briefly as "DN-1417".

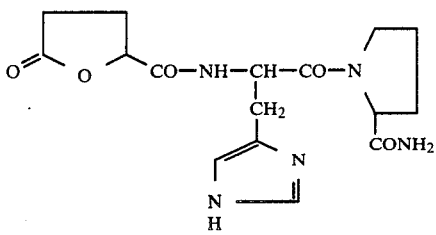

Furthermore, as the polypeptide, there may be mentioned luteinizing hormone-releasing hormone (hereinafter referred to briefly as "LH-RH") or peptides which have the LH-RH activity and have the formula (II).

(Pyr)Glu-$R_1$-Trp-Ser-$R_2$-$R_3$-$R_4$-Arg-Pro-$R_5$ (II)

[wherein $R_1$ stands for His, Tyr, Trp or p-$NH_2$-Phe; $R_2$ stands for Tyr or Phe; $R_3$ stands for Gly or a D-amino acid residue; $R_4$ stands for Leu, Ile or Nle; $R_5$ stands for Gly-NH-$R_6$ ($R_6$ stands for H or a lower alkyl group which may optionally have a hydroxyl group) or NH-$R_6$ ($R_6$ is as defined above)] [U.S. Pat. Nos. 3,853,837, 4,008,209, 3,972,859, British Pat. No. 1,423,083, Proceedings of the National Academy of Science of the United States of America, vol. 78, pp. 6509–6512 (1981)].

As examples of the D-amino acid residue $R_3$ there may be mentioned the residues of alpha-D-amino acids containing up to 9 carbon atoms (e.g. D-Leu, Ile, Nle, Val, Nval, Abu, Phe, Phg, Ser, Thr, Met, Ala, Trp, α-Aibu, etc.), which may have suitable protective groups (e.g. t-butyl, t-butoxy, t-butoxycarbonyl, etc.). Of course, salts of peptide (II) with acids as well as metal complex compounds of peptide (II) may also be employed, just as peptide (II). All abbreviations, wherever they are used in this specification to denote amino acids, peptides, protective groups, etc., are those according to IUPAC-IUB Commission on Biochemical Nomenclature or those commonly employed in the particular field of art. Where any of the amino acids named herein is subject to optical isomerism, all references to such amino acid mean the L-form unless otherwise indicated.

In the present specification, the polypeptide (II) in which $R_1$=His, $R_2$=Tyr, $R_3$=D-Leu, $R_4$=Leu, $R_5$=NH$CH_2$—$CH_3$ is referred to briefly as TAP-144.

Examples of said polypeptide include insulin, somatostatin, somatostatin derivatives (U.S. Pat. Nos. 4,093,573, 4,100,117, 4,253,998), growth hormone, prolactin, adrenocorticotrophic hormone (ACTH), melanocyte stimulating hormone (MSH), thyrotropin releasing hormone (TRH), its salts or its derivatives [U.S. Pat. Nos. 3,957,247, 4,100,152.], thyroid stimulating hormone (TSH), luteinizing hormone (LH), follicle stimulating hormone (FSH), vasopressin, vasopressin derivatives {desmopressin [Folia Endocrinologica Japonica, 54, 5, pp. 676–691, 1978]}, oxytocin, carcitonin, parathyroid hormone, glucagon, gastrin, secretin, pancreozymin, cholecystokinin, angiotensin, human placental lactogen, human chorionic gonadotropin (HCG), enkephalin, enkephalin derivatives [U.S. Pat. No. 4,277,394; European Patent Application Publication No. 31567], endorphin, interferon (α, β, γ), urokinase, kallikrein, thymopoietin, thymosin, motilin, dynorphin, bombesin, neurotensin, caerulein, bradykinin, substance P, kyotorophin and nerve growth factor, peptide type antibiotics such as polymyxin B, colistin, gramicidin, bacitracin, peptide type anti-tumor agents such as bleomycin, neocarzinostatin.

The polysaccharide drugs mentioned above include, among others, heparin and such antitumor agents as lentinan, zymosan and PS-K (krestin).

The aminoglycoside antibiotics mentioned above include, among others, gentamycin, streptomycin, kanamycin, dibekacin, paromomycin, kanendomycin, lipidomycin, tobramycin, amikacin, fradiomycin and sisomicin.

The beta-lactam antibiotics mentioned above include, among others, penicillins such as sulbenicillin, mecillinam, carbenicillin, piperacillin and ticarcillin, thienamycin, and cephalosporins such as cefotiam, cefsulodine, cefmenoxime, cefmetazole, cefazolin, cefotaxime, cefoperazone, ceftizoxime and moxalactam.

The nucleic acid drugs mentioned above include, among others, citicoline and such antitumor agents as cytarabine and 5-FU (5-fluorouracil).

Examples of the cyclodextrin used according to this invention include various cyclodextrins obtainable by hydrolysis of starch with acid or amylase and various cyclodextrin derivatives.

Such cyclodextrins include α(degree of polymerization 6), β(degree of polymerization 7) and γ(degree of polymerization 8) cyclodextrins [Farumashia vol. 16, No. 1 (1980), 33 Yakugaku Zasshi vol. 101 (10), 857–873 (1981), and Japanese Patent Application Publication Sho No. 53 (1978)-31223]. Examples of said cyclodextrin derivatives include tri-O-methylcyclodextrin [Chemical & Pharmaceutical Bulletin 28, 1552–1558 (1980)], triaminocyclodextrin [Angewandte Chemie: International Edition in English 19, 344–362 (1980)] and so forth. In the practice of this invention, α-cyclodextrin is particularly preferable.

The pharmaceutical composition of the present invention is formed into a nasal, vaginal or rectal preparation.

In the nasal preparation, the physiologically active polypeptide is contained as the drug.

The nasal preparation according to the present invention can be produced by the per se conventional processes. For example, small amounts of a pH adjusting agent, preservative, thickening agent (natural gums, cellulose derivatives, acrylic acid polymers, vinyl polymers, etc.) or/and excipient is/are incorporated.

The nasal preparation of the present invention may take a solid, liquid or semi-solid form. In the case of a solid form, the above components may be simply blended or be freeze-dried to provide a powdery composition, the preferred particle size in either case being about 20 to 250 microns. In the case of a liquid preparation, it is preferably an aqueous solution, an aqueous suspension or an oil suspension. The semi-solid preparation is preferably an aqueous or oleaginous gel or ointment.

As to the proportion of each component in the nasal preparation, the polypeptide content of the final preparation is about 0.005 to 50 w/v % and preferably about 0.01 to 30 w/v %, and the proportion of cyclodextrin is about 2 to 99.995 w/v % and preferably about 5 to 99.99 w/v %. In the case of a liquid or semi-solid preparation, the amount of the polypeptide in the preparation is about 0.001 to 50 w/v % and preferably about 0.05 to 40 w/v %, while the amount of cyclodextrin is about 0.5 to 50 w/v % and preferably about 1 to 30 w/v %.

The solid preparation can be produced by the per se known procedure. For example, a mixer is charged with cyclodextrin or, if required, a mixture of cyclodextrin and an excipient and, then, the polypeptide dissolved in a small amount of water is gradually added and mixed in. Thereafter, the mixture is dried in vacuo at a suitable temperature and the dried composition is pulverized to give a solid preparation. Alternatively, the polypeptide and cyclodextrin, plus an excipient if required, are dissolved well in water and freeze-dried or spray-dried to give a dehydrated composition which is then pulverized into a solid preparation.

The excipient is exemplified by glucose, mannitol, inositol, sucrose, lactose, fructose, starch, corn strach, microcrystalline cellulose, hydroxypropylcellulose, hydroxypropylmethyl-cellulose, polyvinyl pyrrolidone, etc.

The liquid preparation can be produced by the per se known procedure. For example, an aqueous preparation for nasal administration can be produced by dissolving, suspending or emulsifying the polypeptide and cyclodextrin in water, a buffer solution or an aqueous medium. The oil suspension for nasal use can be produced by suspending or emulsifying the polypeptide and cyclodextrin in an oleaginous base. The buffer solution is exemplified as those mentioned above.

The above-mentioned oleaginous basis is exemplified by various oils and fats such as sesame oil, olive oil, corn oil, soybean oil, cotton-seed oil, peanut oil, lanoline, vaseline, paraffin, coparaffinate, silicone oil, glycerin fatty acid having 6 to 30 carbon atoms or its glycerin ester or its alcoholic ester, or a mixture thereof.

As to the semi-solid preparation, an aqueous or oleaginous gel or ointment can be produced by the per se conventional procedure. For example, such an aqueous gel for nasal administration can be produced in the following manner. First, an aqueous solution or suspension of cyclodextrin is prepared and, if required, a pH adjusting agent, a preservative or/and the like are added. The solution is divided into halves and an aqueous gel base is dissolved or dispersed in one of the halves and heated or cooled to give a stable gel. In the other half is dissolved the polypeptide. Then, the two halves are combined and evenly mixed to give an aqueous gel preparation.

Adjustment of the pH of preparation can be effected by adding an acid, a base, a buffer solution or the like in the course of production of the preparations. As examples of the acid, there may be mentioned inorganic acids (e.g. hydrochloric acid, boric acid, phosphoric acid, carbonic acid, bicarbonic acid, etc.), amino acids and organic acids (e.g. monocarboxylic acids, oxycarboxylic acids, polycarboxylic acids). The base is exemplified by sodium hydroxide, potassium hydroxide, sodium hydrogen carbonate, sodium carbonate, etc. The buffer solution is exemplified by those mentioned above.

Examples of the aqueous gel basis include natural gums (e.g. gum tragacanth, gum acasia, gum karaya, Irish moss, gum guaiac, gum xanthane, locust bean gum, etc.), cellulose derivatives (e.g. methylcellulose, carboxymethylcellulose, etc.), acrylic acid polymers (e.g. polyacrylic acid, polymethacrylic acid, etc.), vinyl polymers (e.g. polyvinyl pyrrolidone, polyvinyl alcohol, polyvinyl methyl ether, carboxypolymethylene, etc.), synthetic polysaccharides (e.g. polysucrose, polyglucose, polylactose, etc.), starch, dextrin, pectin, sodium alginate, etc. These bases may be used in the form of appropriate mixtures of two or more species.

The oleaginous ointment for nasal administration can be produced by dispersing the polypeptide and cyclodextrin evenly in a hot melt of an oleaginous base and cooling the same under stirring. The oleaginous base may be one of those mentioned hereinbefore.

Preservatives may be incorporated in the nasal preparations. Examples of such preservatives include phenolic compounds such as phenol, cresol, etc.; alcohols such as chlorobutanol, phenylethyl alcohol, propylene glycol, etc.; invert soaps such as benzalkonium chloride, benzethonium chloride, etc.; benzoic acid, sorbic acid, dehydroacetic acid and sulfurous acid and salts thereof; acids and their salts such as sodium hydrogen sulfite.

The nasal preparation of this invention, if it is a solid preparation, can be administered by the following exemplary procedure. Thus, a capsule containing the powdery preparation is set in an exclusive dust applicator equipped with needles to pierce the capsule at the top and bottom thereof and an air balloon is used to drive the powdery contents into the nasal cavity.

In the case of a liquid preparation, it is put in a nasal douche, an atomizer or a spray-mist applicator suited for nasal application of liquids and dripped or sprayed into the nasal cavity.

The semi-solid preparation can be administered, for example by filling a tube with the preparation and sending the preparation directly into the nasal cavity through an applicator attached to the mouth of the tube or by administering the indicated dose of the preparation by means of a nasal insertion device.

The dosage of the polypeptide varies with its kind, the disease to be managed and the animals to be treated (e.g. warm-blooded mammalian animals such as rat, rabbit, horse, cattle, human). The proper amount of the solid preparation per dose is about 5 mg to 100 mg, that of the liquid preparation is about 0.05 ml to 0.5 ml, and that of the semi-solid preparation is about 50 mg to 500 mg. The nasal preparation may be administered once to four times per day.

By the administration of the nasal preparation of this invention, it brings the follwing advantageous features.

(1) The physiologically active polypeptide which is poorly absorbed through the gastrointestinal tract can be administered by a route other than injection to achieve an improved bioavailability.

(2) The physiologically active polypeptide can be administered without accompanying pain.

(3) Self-medication at home is possible. This is especially beneficial when repeated administration is necessary.

(4) Cyclodextrin as an absorption promoting component is tasteless, odorless, only slightly toxic and not irritating to the mucous membrane, thus permitting production of pharmaceutical preparations which can be safely used in repeated dose regimens.

In the vaginal preparation of the present invention, the physiologically active polypeptide mentioned above is contained as the drug.

The pharmaceutical preparation for vaginal administration according to this invention can be produced by per se conventional processes.

The pharmaceutical preparation for vaginal administration according to this invention may have, among others, the form of a vaginal suppository which retains its solid form at room temperature and melts at the body temperature, or the form of an ointment or liquid contained in a tube, for instance. In the former case, the preparation of solid form is vaginally administered, and the preparation is melted at the body temperature. In the latter case, the tube containing the ointment or liquid is vaginally administered, and the contents are pushed out and the tube is taken out.

The preparation may also be made available in the form of a tablet which, after administration, is dissolved or disintegrated in the vaginal fluid. In this case, the preparation can be easily administered into the vagina when an adequate device, preferably an inserter, is used.

The vaginal suppository or ointment can be produced by the per se known processes, for instance by dissolving or dispersing a physiologically active polypeptide and cyclodextrin in a preliminarily molten oleaginous or aqueous base, attaining homogeneous dispersion by adequate warming and stirring, and molding the mixture.

In the preparation for vaginal administration, any of the known suppository bases or ointment bases can be employed. As the water-soluble bases, there may be mentioned polyethylene glycols (e.g. those having the mean molecular weight of 200, 300, 400, 1000, 4000, 6000), propylene glycol, glycerol. These bases may be used either alone or as a mixture. As examples of said oleaginous bases there may be mentioned such oils and fats as sesame oil, olive oil, corn oil, soybean oil, cottonseed oil, peanut oil, cacao butter, castor oil, wool fat, squalene, etc., the corresponding modified materials as modified by such procedures as hydrogenation, fatty acid interchange, acetylation, fractional extraction, etc.; mineral oils such as vaseline, paraffin, silicone oil, etc.; glycerin esters of fatty acids of 6 to 30 carbon atoms, particularly higher fatty acid esters such as glycerin palmitate, glycerin laurate, glycerin stearate, glycerin myristate, etc.; esters of fatty acids of 6 to 30 carbon atoms with alcohols of 2 to 8 carbon atoms, particularly waxes such as isopropyl myristate, butyl stearate, diisopropyl adipate, diethyl sebacate, etc.; and higher fatty acids of 6 to 30 carbon atoms, particularly stearic acid, oleic acid, etc. Such oleaginous bases may be used either alone or as a mixture.

To the aqueous pharmaceutical preparation for vaginal administration in accordance with the present invention, there may be added, if necessary, an isotonizing agent (e.g. sodium chloride, potassium chloride, sorbitol), a wetting agent (e.g. glycerol, propylene glycol), a preservative (e.g. benzyl alcohol), a pH-adjusting agent (e.g. hydrochloric acid, acetic acid, citric acid, phosphoric acid, sodium hydroxide, potassium hydroxide, ammonia, a salt of any of these), a thickening agent (e.g. methylcellulose, carboxymethylcellulose), a stabilizer (e.g. sodium ethylenediaminetetraacetate, human serum albumin, citric acid), a dispersing agent [e.g. lecithin, Tween (polyoxyethylenesorbitan fatty acid ester, Kao-Atlas Co., Ltd. Japan), Span (higher fatty acid sorbitan ester, Kao-Atlas Co.)], and so on.

The preparation of the present invention for vaginal administration may be a gel suppository prepared by a per se conventional manner from an aqueous solution or suspension containing the present polypeptide by adding a water-soluble gel-forming base. As examples of the water-soluble gel bases, there may be mentioned naturally occurring gums (e.g. gum tragacanth, gum acacia, karaya gum, Irish moss, gum guaiac, gum xanthane, locust-bean gum, etc.), cellulose derivatives (e.g. methylcellulose, carboxymethylcellulose, etc.), acrylic acid polymers (e.g. polyacrylic acid, polymethacrylic acid, etc.), vinyl polymers (e.g. polyvinyl pyrrolidone, polyvinyl alcohol, polyvinyl methyl ether, carboxypolymethylene, etc.), synthetic polysaccharides (e.g. polysucrose, polyglucose, polylactose, etc.), starch, dextrin, pectin, sodium alginate and so forth. These bases may be employed either singly or, if necessary, as a mixture of two or more different bases, and copolymers of the polymer mentioned above are also employed.

The aqueous solution of the preparation for vaginal administration is also vaginally administered as supported on a solid matrix, for instance. The solid matrix may be one of the known matrixes such as porous materials made of high molecular compounds (e.g. silicon rubber, polyurethane, etc.), biological polymers (e.g. collagen, gelatin, etc.), cellulosic materials (e.g. cotton, paper, etc.) and so forth.

The preparation of solution may be made to foam or aerosol by a per se conventional manner.

To prepare vaginal tablets, the active component is compressed into appropriate dosage units generally by a procedure analogous to the known procedure, using a diluent such as lactose, sucrose, starch, etc., disintegrating agents such as starch, sodium hydrogen carbonate, etc.; binders such as starch, gelatin, carboxymethylcellulose, polyvinylpyrrolidone, hydroxypropylcellulose, etc.; lubricants such as talc, magnesium stearate, polyethylene glycol (6000), stearic acid, etc. When the required dosage is very small, an increased product uniformity may be obtained by preparing a mixed solution of the polypeptide with a diluent such as lactose, starch or mannitol beforehand, then drying the mixed solution by way of freeze-drying or spray-drying to make a diluted powder, and molding this diluted powder into tablets. In view of the relative scarcity of vaginal fluids as compared with gastrointestinal fluids, disintegration and dissolution are important considerations.

To assist in disintegration and dissolution, there may be prepared effervescent tablets with a combination of alkali metal carbonates (e.g. sodium carbonate) or bicarbonates with citric acid or tartaric acid.

Tablets thus prepared can be inserted into the vagina as they are.

The aqueous solution or aqueous suspension containing cyclodextrin and a physiologically active polypeptide both dissolved or dispersed therein may also serve as the pharmaceutical preparation for vaginal administration according to this invention.

The content, in the pharmaceutical preparation, of the polypeptide depends on the kind of the polypeptide, the pharmacological effect desired, the number of administrations, the interval between administrations, the severity of the disease, and other factors. However, it may be at any level which is sufficient for the development of the desired pharmacological effect. Thus, an adequate content can be selected, for instance, within the range of about 0.000025% to 90% by weight, preferably within the range of 0.0001% to 50% by weight, based on the composition according to this invention.

The addition level or concentration of cyclodextrin in a solid preparation is generally about 1 to 90% by weight, preferably about 2 to 50% by weight. In the case of a liquid or semi-solid preparation, the level is generally about 0.5 to 50% by weight, preferably about 1 to 30% by weight. In each case, it is especially preferable that the concentration is about 2 to 20% by weight.

The single dose of the pharmaceutical preparation for vaginal administration may vary depending on the form of the preparation, the kind of the principal drug (i.e. physiologically active polypeptide), the animal to be treated (e.g. warm-blooded mammalian animals such as rat, rabbit, horse, cattle, human) and the purpose of administration. The only requirement is that the principal drug should be administered in an effective dose. Thus, an adequate single dose can be selected, for instance within the range of about 1 mg to 10 g, preferably about 20 mg to 2 g. The number of administrations per day may also vary in the manner mentioned above but can be adequately selected from among once to three times.

The administration of the pharmaceutical preparation for vaginal administration according to this invention, brings about the following characteristic features: (1) Those physiologically active polypeptides that are hardly absorbed through the gastrointestinal tract can be administered by a route other than injection and at the same time a high level of bioavailability can be attained. Accordingly, the desired pharmacological effect can be obtained with a small dose of said polypeptide. (2) Physiologically active polypeptides can be administered expediently without any accompanying pain. (3) In cases where frequent repeated administration is necessary, for instance in cases where the treatment of congenital metabolic disorder is contemplated or a contraceptive or anti-tumor action is expected, the pharmaceutical preparation according to this invention can be easily administered to the patient by self-medication, and thus it enables therapy at home. (4) Since a sustained drug level in the blood is obtainable as compared with injections, the release of the polypeptide from the preparation can be easily controlled and if desired, a further sustained pharmacological effect can be obtained. (5) Even if the vaginal mucous membrane is the site of action, an efficient pharmacological effect can be expected. (6) Cyclodextrin used as an absorption-promoting component is only slightly toxic and only slightly irritating to the mucous membrane, thus it permits the production of pharmaceutical preparations which can be safely used in repeated administrations.

In the present rectal preparation, the hydrophilic drug which is poorly absorbable through the gastrointestinal tract is contained as the drug.

The rectal preparation according to this invention can be produced by per se known processes. For example, the drug and cyclodextrin are added to an oleaginous or aqueous base and the mixture is warmed to an adequate temperature (about 40° to 60° C.) for dissolution or dispersion, then poured into a mold and cooled (about 10° to 25° C.).

The above-mentioned oleaginous base is, for example, a higher fatty acid glyceride [e.g. cacao butter, which is of the natural origin, Witepsols (Dynamite Nobel, Federal Republic of Germany) (which is a semisynthetic base)], a medial fatty acid glyceride [e.g. Miglyols (Dynamite Nobel)] or a vegetable oil (e.g. sesame oil, soybean oil, corn oil, cottonseed oil, olive oil).

The aqueous base mentioned above includes, among others, polyethylene glycols, polypropylene glycols and glycerin as well as hydrogel bases such as natural gum (e.g. gum tragacanth, gum arabic, karaya gum, Irish moth, gum guaiac, xanthan gum, locust bean gum), cellulose derivatives (e.g. methylcellulose, carboxymethylcellulose), acryl polymers (e.g. polyacrylic acid, polymethacrylic acid), vinyl polymers (e.g. polyvinylpyrrolidone, polyvinyl alcohol, polyvinyl methyl ether, carboxypolymethylene), synthetic polysaccharides (e.g. polysucrose, polyglucose, polylactose), starch, dextrin, pectin and sodium alginate.

These bases may be used either alone or in the form of a mixture of two or more of them.

In producing the pharmaceutical preparation for rectal administration according to this invention, small amounts of preservatives, pH adjusting agents, thickening agents and/or excipients may be incorporated.

The preservatives include, for example, alcohols such as chlorobutanol, quaternary ammonium salts such as benzalkonium chloride, benzethonium chloride and cetrimide, sorbic acid and chlorhexidines.

The pH adjusting agents include inorganic acids such as hydrochloric acid, boric acid, phosphoric acid, carbonic acid and bicarbonic acid, organic acids inclusive of mono- and polycarboxylic acids, and amino acids as well as bases such as sodium hydroxide, potassium hydroxide, sodium hydrogen carbonate and sodium carbonate.

As the buffer solution, there may be mentioned those mentioned above.

The thickening agents include, for example, natural gums such as xanthan gum and locust bean gum, cellulose derivatives such as methylcellulose and carboxymethylcellulose, acrylic acid polymers such as polyacrylic acid, and vinyl polymers such as polyvinylpyrrolidone and polyvinyl alcohol.

In this manner, the pharmaceutical preparation for rectal administration is produced in the form of solid preparation (e.g. oleaginous suppository, water-soluble suppository), a semi-solid preparation (e.g. ointment suppository, gel or jelly suppository), suspension (e.g. rectal capsule or enema containing an oleaginous or water-soluble vehicle and the drug), or liquid preparation (e.g. rectal capsule or enema containing an oleaginous or water-soluble vehicle and the drug), for instance.

The effective single dose of the drug used in accordance with this invention may vary depending on the kind of the drug and the conditions of the animal to be treated. A peptide drug is used, for example in a dose of about 25 μg to 250 mg, a polysaccharide drug in a dose of about 500 mg to 2,000 mg, for instance, an aminoglycoside or beta-lactam antibiotic in a dose of, for example, about 50 to 1,000 mg, and a nucleic acid drug in a dose of about 20 to 1,000 mg, for instance.

The addition level of cyclodextrin in the preparation is generally 1 to 50 w/w percent, preferably about 2 to 20 w/w percent, most preferably about 2 to 10 w/w percent.

These preparations can be administered rectally by direct insertion into the anus of the animals to be treated (e.g. warm-blooded mammalian animals such as rat, rabbit, horse, cattle, human). Semi-solid, foamy or liquid preparations can also be administered by using an inserter. The rectal preparation may be administered once to three times per day.

The administration of the present rectal preparation brings about the following advantageous features:

(1) Since the rate of absorption of the drug into the body is improved, a smaller dose of the drug can exert its effect efficiently.

(2) The preparation can be expediently administered without substantial accompanying pain.

(3) Self-medication at home is possible. This is beneficial when repeated administration is necessary.

(4) The blood level of the drug can be sustained through sustained release thereof from the preparation and therefore the drug efficacy can be maintained longer as compared with injections.

(5) Cyclodextrin used as an absorption promoting component is only slightly toxic and only slightly irritating to the mucous membrane. Thus it permits production of pharmaceutical preparations which can be safely used in repeated dose regimens.

(6) In contrast with nasal administration, the present preparation can be practiced with those drugs that are to be administered in large doses or have unpleasant taste. The present preparation can also be practiced with those drugs that are unstable in aqueous bases, by using oleaginous bases.

The following Experimental Examples and Examples are further illustrative of this invention.

EXPERIMENTAL EXAMPLE 1

Male SD strain rats (body weights 250 g, approx.) fasted for 16 hours are used in groups of at least 3 animals. Each animal is anesthetized with pentobarbital and administered nasal medication in accordance with the method described in International Journal of Pharmaceutics 7, 317 (1981). Then, 0.1 ml/kg of insulin solution is directly administered into the nasal cavity with a micropipette via the nostril. Blood samples are taken from the tail vein at timed intervals and the plasma glucose levels are determined.

The insulin solution used is a mixed solution of 10 U or 20 U of porcine insulin (about 0.2 mg or 0.8 mg) and 0 mg to 10 mg [which correspond to 0 to 10%] of $\alpha$-, $\beta$- or $\gamma$-cyclodextrin in 0.1 ml of an isotonic buffer solution (pH 7.4). In the case of $\beta$-cyclodextrin whose saturation solubility is about 1.8%, it is administered as suspensions when its concentrations are over the above solubility limit.

As control, insulin is intravenously administered and plasma glucose levels are determined in the manner as above.

The results are shown in Table 1. As shown in Table 1, the addition of $\alpha$-, $\beta$- or $\gamma$-cyclodextrin causes a remarkable depression of plasma glucose level as compared with the control, indicating that insulin is efficiently absorbed through the nasal mucous membrane.

TABLE 1

| | | Change in plasma glucose level after nasal administration of insulin to rats | | | | | |
|---|---|---|---|---|---|---|---|
| | | Dose of insulin U/Kg | Kind and concentration of cyclodextrin | Change (%) in plasma glucose level | | | |
| | Route | | | Before administration | 1 hr. | 2 hr. | 4 hr. |
| Control | Intravenous | 5 | — | 100 | 29.6 | 31.6 | 41.7 |
| | Intranasal | 10 | — | 100 | 93.7 | 99.3 | 103.0 |
| | Intranasal | 20 | — | 100 | 92.4 | 90.6 | 99.9 |
| This invention | Intranasal | 10 | $\alpha$, 3% | 100 | 73.5 | 59.7 | 62.9 |
| | Intranasal | 10 | $\alpha$, 5% | 100 | 59.4 | 46.8 | 54.4 |
| | Intranasal | 10 | $\alpha$, 10% | 100 | 33.8 | 24.8 | 40.3 |
| | Intranasal | 20 | $\alpha$, 5% | 100 | 64.3 | 38.4 | 47.9 |
| | Intranasal | 10 | $\beta$, 10% | 100 | 62.5 | 48.6 | 49.7 |
| | Intranasal | 10 | $\gamma$, 10% | 100 | 80.0 | 81.0 | 74.2 |

EXPERIMENTAL EXAMPLE 2

THE 2 mg/kg equivalent of $^{14}$C-DN-1417 and 5 mg (5% equivalent) of $\alpha$-cyclodextrin are dissolved in 0.1 ml of physiological saline and 0.1 ml of the solution is administered into the nasal cavity of each rat with a micropipette in the manner of Experimental Example 1. Blood samples are taken from the tail vein at timed intervals and the total radioactivity in the plasma is measured to ascertain the blood concentration. As controls, the same dose is given subcutaneously or $^{14}$C-DN-1417 alone without addition of $\alpha$-cyclodextrin, is administered similarly.

The results are shown in Table 2. It is apparent that the nasal administration of the preparation according to this invention causes marked increases in the absorption of the peptide and that as compared with subcutaneous administration, the bioavailability of the peptide is increased about 5-fold from about 10% to about 50%.

TABLE 2

| | Concentration of DN-1417 in plasma after nasal administration of DN-1417 (2 mg/kg) to rats | | | | |
|---|---|---|---|---|---|
| | | Content of cyclodextrin | Concentration in plasma $\mu$g/ml | | |
| | Route | | 1 hr. | 2 hr. | 4 hr. |
| Control | Subcutaneous | — | 2.3 | 1.6 | 0.76 |
| | Intranasal | — | 0.22 | 0.21 | 0.23 |
| This invention | Intranasal | $\alpha$, 5% | 1.3 | 1.0 | 0.51 |

EXPERIMENTAL EXAMPLE 3

In 0.1 ml of physiological saline are dissolved 100 $\mu$g of TAP-144 and 5 mg of $\alpha$-cyclodextrin, and in the manner of Experimental Example 1, the 0.1 ml/kg equivalent of the solution is administered into the nasal cavity (the dose of TAP-144: 100 $\mu$g/kg). Blood samples are taken from the tail vein at timed intervals and the serum concentration of TAP-144 is determined by radioimmunoassay. Control animals are either subcutaneously injected at the same dose or given nasally a similar preparation which does not contain $\alpha$-cyclodextrin.

The results are shown in Table 3. It is apparent that the nasal administration of the composition of this invention results in a marked increase in the absorption of the peptide and that as compared with subcutaneous administration, the bioavailability of the drug is increased about 3.5 times from about 20% to about 70%.

TABLE 3

| | Concentration of TAP-144 in serum after nasal administration of TAP-144 (100 $\mu$g/kg) to rats | | | | | |
|---|---|---|---|---|---|---|
| | | Cyclo-dextrin | Concentration in Serum ng/ml | | | |
| | Route | | 0.5 hr. | 1 hr. | 2 hr. | 4 hr. |
| Control | Subcutaneous | — | 44.0 | 40.2 | 24.0 | 6.7 |
| | Intranasal | — | 3.2 | 3.9 | 3.5 | 3.9 |
| This invention | Intranasal | $\alpha$, 5% | 32.1 | 30.3 | 16.4 | 6.8 |

EXPERIMENTAL EXAMPLE 4

SD-strain mature female rats (weighing about 270 g, 14 to 18 weeks old, in groups of 4 to 5 individuals) at diestrus as selected by the vaginal smear test covering a period of at least one week are anesthetized with pentobarbital and phenobarbital at 8–11 a.m., and a solution prepared by dissolving 500 μg of TAP-144 and 20 mg (2%), 50 mg (5%) or 100 mg (10%) of α-cyclodextrin in physiological saline in an amount to make 1 ml is administered into the vagina with about 12 mg of cotton soaked therewith at the dose level of 0.2 ml/kg (corresponding 100 μg/kg of TAP-144). Blood samples are taken from the tail vein at timed intervals and assayed for the serum TAP-144 level by radioimmunoassay [refer to Endocrinologia Japonica, vol. 27, pages 593–605 (1980)]. In control runs, the same dose of TAP-144 is intravenously administered or a similar preparation produced without the addition of α-cyclodextrin is vaginally administered, and the serum level is determined.

The results shown in Table 4 indicate that the vaginal absorption of TAP-144 administered as the α-cyclodextrin-containing preparation is promoted about 6 times as compared with the control vaginal preparation, and that a high serum level is maintained longer than the case with the control intravenous administration run.

TABLE 4

| | | Concentration of α-cyclodextrin | Concentration of TAP-144 in serum (ng/ml) Time after administration | | | | | | |
|---|---|---|---|---|---|---|---|---|---|
| | Route | | 5 min. | 10 min. | 30 min. | 1 hr. | 2 hr. | 4 hr | 6 hr. |
| Control | Intravenous | — | 212 | 173 | 74.2 | 39.3 | 6.76 | 1.83 | <0.13 |
| | Intravaginal | 0% | — | — | 4.75 | 4.98 | 5.37 | 7.98 | 5.94 |
| This invention | Intravaginal | 2% | — | — | 28.1 | 33.8 | 39.2 | 32.1 | 23.5 |
| | Intravaginal | 5% | — | — | 32.1 | 44.3 | 40.2 | 24.1 | 10.5 |
| | Intravaginal | 10% | — | — | 45.3 | 75.3 | 71.1 | 32.7 | 12.5 |

EXPERIMENTAL EXAMPLE 5

Following the procedure of Experimental Example 4, a suspension of 5% β-cyclodextrin (β-CD) in physiological saline (containing 100 μg/kg/0.2 ml of TAP-144), a 5% methylcellulose jelly preparation containing 5% α-cyclodextrin (α-CD) (containing 100 μg/kg/400 mg of TAP-144) and an oleaginous suppository (base: Witepsol, containing 100 μg/kg/200 mg of TAP-144) are vaginally administered to rats (in groups of 4 to 5 individuals) under anesthetization, and the serum TAP-144 level determination is performed.

The results shown in Table 5 indicate that inclusion of α-cyclodextrin produces an evident absorption-promoting effect.

TABLE 5

| Preparation | Kind and concentration of cyclodextrin | Concentration of TAP-144 in serum (ng/ml) Time after administration (hour) | | | | |
|---|---|---|---|---|---|---|
| | | 0.5 | 1 | 2 | 4 | 6 |
| Control Physiological saline | 0% | 4.75 | 4.98 | 5.37 | 7.98 | 5.94 |
| This invention 5% methylcellulose jelly | α-CD, 5% | 20.1 | 23.9 | 21.0 | 16.1 | 10.3 |
| Oil suppository | α-CD, 5% | 14.5 | 19.7 | 20.3 | 29.9 | 20.2 |
| Physiological saline | β-CD, 5% | 18.4 | 15.0 | 20.2 | 20.6 | 16.3 |

As is evident from the foregoing, administration in the form of the pharmaceutical preparation according to this invention makes it possible for a highly active LH-RH derivative such as TAP-144 to be absorbed into the body in an efficient manner. Therefore, it is expected that the pharmaceutical preparation according to this invention can be used in expedient drug administration for the purpose of treating breast cancer, which inevitably requires prolonged administration [Lancet, vol. 1, pages 1213–1216 (1982)], or of contraception through shortening of the luteal phase [Science, vol. 215, pages 170–172 (1982)], for instance.

EXPERIMENTAL EXAMPLE 6

Following the procedure of Experimental Example 4, a solution of porcine insulin and 5% α-cyclodextrin (α-CD) in physiological saline (containing 20 units of porcine insulin/kg/0.2 ml) is vaginally administered to rats. Blood samples are taken from the tail vein at timed intervals and assayed for the plasma glucose level. The plasma glucose level just before administration of insulin is expressed as 100%. In control studies, an α-cyclodextrin-free physiological saline solution of insulin is administered either subcutaneously (5 units/kg) or intravaginally (20 units/kg) and the plasma glucose level is determined in the same manner.

The results shown in Table 6 indicate that when insulin is administered intravaginally as the α-cyclodextrin-containing pharmaceutical preparation for vaginal administration according to this invention, a marked decrease in the plasma glucose level is obtained as compared with the control vaginal administration group, the reduction in the area under the plasma glucose level-time curve within 6 hours after administration being $339.9 \pm 11.2$ (mean±standard error) %×hour for the invention group and $158.2 \pm 29.6$ (mean±standard error) %×hour for the control group; in this case the pharmacological effect is almost doubled. When compared with the control subcutaneous administration group, a prolonged hypoglycemic effect is obtained in the invention group.

TABLE 6

| | Route | Dose of insulin (Unit/kg) | Plasma glucose level just before the administration (%) | Plasma glucose level (%) Time after the administration (hour) | | | | | |
|---|---|---|---|---|---|---|---|---|---|
| | | | | 0.5 | 1 | 2 | 3 | 4 | 6 |
| Control | Subcutaneous | 5 | 100 | 67.0 | 54.7 | 42.2 | 35.1 | 37.5 | 74.1 |
| | Intravaginal (physiological saline) | 20 | 100 | 80.7 | 75.8 | 77.2 | 74.2 | 66.9 | 67.8 |
| This invention | Intravaginal (5% α-CD) | 20 | 100 | 66.5 | 52.7 | 40.0 | 33.7 | 31.4 | 41.5 |

EXPERIMENTAL EXAMPLE 7

Male SD strain rats (body weights, approx. 300 g) fasted in advance are used in groups of 3 individuals. Under pentobarbital anesthetization, each animal is rectally given 0.1 ml of a $^{14}$C-DN-1417 preparation [solution or suspension of 0.6 mg of $^{14}$C-DN-1417 and 5 mg of α- or β-cyclodextrin in 0.1 ml of an isotonic hydrochloric acid-potassium chloride buffer (pH 3.0)] by means of a micropipet. Blood samples are taken from the tail vein at timed intervals and the plasma level is determined from the total radioactivity in the blood. In the control group, $^{14}$C-DN-1417 is administered in the same manner but without the addition of cyclodextrin. The results, which are shown in Table 7, indicate that the plasma level is markedly increased as compared with the control group. It is thus evident that $^{14}$C-DN-1417 is absorbed efficiently through the rectum.

TABLE 7

| Level of addition of cyclodextrin | Plasma level (μg/ml) | | | | | | | AUC* (0–6 hr.) |
|---|---|---|---|---|---|---|---|---|
| | 0.08 | 0.25 | 0.5 hr. | 1 hr. | 2 hr. | 4 hr. | 6 hr. | |
| Control | 0.21 | 0.25 | 0.25 | 0.30 | 0.22 | 0.21 | 0.23 | 1.40 |
| This invention | | | | | | | | |
| 5% (w/v) α-cyclodextrin | 0.17 | 1.15 | 1.36 | 1.06 | 0.68 | 0.66 | 0.71 | 4.61 |
| 5% (w/v) β-cyclodextrin | — | 0.62 | 0.68 | 0.54 | 0.33 | 0.23 | 0.28 | 2.06 |

*(Note) AUC: Area under the plasma level-time curve (μg · hr/ml)

EXPERIMENTAL EXAMPLE 8

DN-1417 with or without 5 mg of α-cyclodextrin is dissolved in 0.1 ml of hydrochloric acid-potassium chloride buffer, pH 3.0. The solution is administered into the rectum of each male SD strain rat (weighing about 250 g, each group containing of 3 individuals) with a micropipet and 60 minutes later, pentobarbital (40 mg/kg) is intraperitoneally injected. The percent reduction in the sleeping time, which is the time interval between the loss of righting reflex and the reaquisition thereof, is determined.

Percent reduction in sleeping time =

$$\left(1 - \frac{\text{Sleeping time after administration of DN-1417}}{\text{Sleeping time after administration of vehicle}}\right) \times 100$$

The results, which are shown in Table 8, indicate that the addition of 5% α-cyclodextrin almost doubles the pharmacological activity of DN-1417 in positive correlation with the increased absorption.

TABLE 8

| | Cyclodextrin addition level | Dose of DN-1417 (mg/kg) | % Reduction in sleeping time |
|---|---|---|---|
| Control | — | 5 | 7.8 |
| | — | 10 | 14.8 |

TABLE 8-continued

| | Cyclodextrin addition level | Dose of DN-1417 (mg/kg) | % Reduction in sleeping time |
|---|---|---|---|
| This invention | 5% (w/v) α-cyclodextrin | 5 | 15.2 |
| | 5% (w/v) α-cyclodextrin | 10 | 26.4 |

EXPERIMENTAL EXAMPLE 9

A Witepsol W-35-based suppository (weight: about 45 mg) containing DN-1417 in an amount corresponding to 2 mg/kg and 5 w/w percent of α- or β-cyclodextrin is administered into the rectum of each male SD strain rat weighing about 90 g (4 weeks of age, each group consisting of 10 individuals), and the discharge rate is examined with a suppository without cyclodextrin used as the control. The results, which are shown in Table 9, indicate that both the α- and β-cyclodextrin-containing suppositories do not differ inthe discharge rate from the control suppositories. This means that the cyclodextrin-added suppositories are hardly irritatable to the rectal mucous membrane.

TABLE 9

| | Base | Cyclodextrin addition level | Rate of discharge** after | | |
|---|---|---|---|---|---|
| | | | 15 min. | 30 min. | 45 min. |
| Control | Witepsol W-35 | — | 3/10 | 3/10 | 3/10 |
| This invention | Witepsol W-35 | 5% (w/w) α-cyclodextrin | 2/10 | 2/10 | 3/10 |
| | Witepsol W-35 | 5% (w/w) β-cyclodextrin | 1/10 | 3/10 | 3/10 |

**The number of animals which discharged the suppository/the number of animals tested

EXPERIMENTAL EXAMPLE 10

Porcine insulin (in an amount corresponding to 50 IU/kg) and 5 mg of α-, β- or γ-cyclodextrin are dissolved in 0.1 ml of physiological saline, the solution is administered into the rat rectum in the manner in Experimental Example 7, and plasma glucose levels are determined at timed intervals. In the control group, porcine insulin is administered in the same manner but without the addition of cyclodextrin.

The results, which are shown in Table 10, indicate that the addition of α-, β- or γ-cyclodextrin results in a greater hypoglycemic effect than in the control group. It is thus evident that insulin is absorbed more efficiency through the rectum.

TABLE 10

| | Change (%) in plasma glucose level | | | | |
|---|---|---|---|---|---|
| Cyclodextrin addition level | Before administration | 0.5 hr. | 1 hr. | 1.5 hr. | 2 hr. |
| Control — | 100 | 102.2 | 86.0 | 95.2 | 121.9 |
| This invention 5% (w/v) α-cyclodextrin | 100 | 92.9 | 39.1 | 39.6 | 69.6 |
| 5% (w/v) β-cyclodextrin | 100 | 94.3 | 70.1 | 76.3 | 90.1 |
| 5% (w/v) γ-cyclodextrin | 100 | 94.8 | 79.0 | 81.3 | 93.0 |

EXPERIMENTAL EXAMPLE 11

A Witepsol W-35-based suppository (weight: about 45 mg) containing porcine insulin in an amount corresponding to 50 IU/kg and 5 w/w percent of α- or β-cyclodextrin is prepared in the conventional manner and administered to each male SD strain rat (body weight: about 300 g; 3 animals per group) after fasting, at the site about 1.5 cm from the anus. Thereafter, blood samples are taken from the tail vein and assayed for the blood sugar level. The results, which are shown in Table 11, indicate that the addition of α- or β-cyclodextrin results in an increased absorption of insulin.

TABLE 11

| | Change (%) in plasma glucose level | | | | | |
|---|---|---|---|---|---|---|
| Cyclodextrin addition level | Before administration | 0.5 hr. | 1 hr. | 1.5 hr. | 2 hr. | 3 hr. |
| Control — | 100 | 98.1 | 94.1 | 97.4 | 98.1 | 102.5 |
| This invention 5% (w/w) α-cyclodextrin | 100 | 93.1 | 61.1 | 63.5 | 86.1 | 93.4 |
| 5% (w/w) β-cyclodextrin | 100 | 87.1 | 81.5 | 80.1 | 92.5 | 100.4 |

EXPERIMENTAL EXAMPLE 12

Heparin sodium 600 U (corresponding to 3.7 mg) and 5 mg of α-cyclodextrin are dissolved in 0.1 ml of physiological saline and the solution is rectally administered to rats in the manner in Experimental Example 7. Blood samples are taken from the tail vein at timed intervals. A 0.27 ml portion of each blood sample is placed in a polyethylene microtube containing 0.03 ml of 3.8 w/v percent of sodium citrate, the tube contents are stirred well and then centrifuged, and the plasma portion is subjected to prothrombin time (blood coagulation time) determination using a thromboplastin reagent (Simplastin, Ono Pharmaceutical Co., Japan). In the control group, the same procedure is followed with α-cyclodextrin-free heparin sodium. The results, which are shown in Table 12, indicate that the addition of α-cyclodextrin results in a prolonged blood coagulation time as compared with the control group. An increased absorption of heparin is thus shown.

TABLE 12

| | | Blood coagulation time (in seconds) | | | | | |
|---|---|---|---|---|---|---|---|
| | Cyclodextrin addition level | Before administration | 0.5 hr. | 0.75 hr. | 1 hr. | 1.5 hr. | 2 hr. |
| Control | — | 13.6 | 14.3 | 13.7 | 14.7 | 15.3 | 14.7 |
| This invention | 5% (w/v) α-cyclodextrin | 14.3 | 17.2 | 18.4 | 19.7 | 18.9 | 19.4 |

EXPERIMENTAL EXAMPLE 13

An amount (corresponding to 50 mg/kg) of 5-FU and 5 mg of α-cyclodextrin are finely milled in a mortar and added to 0.1 ml of physiological saline. The mixture is subjected to ultrasonic treatment (27 KHz, 5 minutes). The thus-obtained suspension is rectally administered to rats in the manner in Experimental Example 7. Blood samples are taken from the tail vein at timed intervals and 5-FU plasma levels are determined by bioassay using *Micrococcus luteus* ATCC-10240 as the test organism. In the control group, the procedure is followed with α-cyclodextrin-free 5-FU. The results, which are shown in Table 13, indicate that the addition of α-cyclodextrin results in an increased absorption of 5-FU as compared with the control group.

TABLE 13

| | | Plasma level (μg/ml) | | | | AUC |
|---|---|---|---|---|---|---|
| | Cyclodextrin addition level | 0.5 hr. | 1 hr. | 2 hr. | 4 hr. | (0–4 hr.) |
| Control | — | 0.97 | 0.43 | 0.13 | 0.06 | 1.1 |
| This invention | 5% (w/v) α-cyclodextrin | 1.37 | 1.72 | 1.05 | 0.49 | 4.0 |

EXPERIMENTAL EXAMPLE 14

An amount (corresponding to 12 mg/kg) of gentamycin sulfate and 50 mg of α-cyclodextrin are added to 1 ml of physiological saline and the mixture is administered into the rectum of a male rabbit weighing about 2.5 kg in the manner in Experimental Example 7. Blood sampling is performed from the auricular vein at timed intervals and the plasma gentamycin level is determined by bioassay using *Bacillus subtilis* PCI 219 as the test organism. In the control study, the same procedure is followed with α-cyclodextrin-free gentamycin sulfate. The results are shown in Table 14. It is indicated that the addition of α-cyclodextrin results in an increased plasma level and in an increased absorption.

TABLE 14

| | | Plasma level (μg/ml) | | | |
|---|---|---|---|---|---|
| | Cyclodextrin addition level | 0.5 hr. | 1 hr. | 2 hr. | 4 hr. |
| Control | — | 0.2 | 0.5 | 0.4 | 0.2 |
| This | 5% (w/v) | 0.7 | 2.5 | 1.7 | 1.2 |

TABLE 14-continued

| Cyclodextrin | Plasma level (μg/ml) | | | |
|---|---|---|---|---|
| addition level | 0.5 hr. | 1 hr. | 2 hr. | 4 hr. |
| invention α-cyclodextrin | | | | |

EXPERIMENTAL EXAMPLE 15

A Witepsol W-35-based suppository (total weight: 150 mg) containing an amount (corresponding to 50 mg/kg) of sodium cefazolin and 10 w/w percent of α-cyclodextrin is prepared by a conventional method and administered to each male SD strain rat (body weight: about 400 g; 3 animals per group) after fasting, at the site about 1.5 cm in from the anus. Thereafter, blood sampling from the tail vein is performed at timed intervals and the plasma cefazolin level is determined by bioassay using *Bacillus subtilis* PCI-219 as the test organism. As the control study, the same experiment is conducted with α-cyclodextrin-free sodium cefazolin. The results are shown in Table 15, from which it can be seen that the addition of α-cyclodextrin results in an increased plasma level, hence an increased absorption, as compared with the control group.

TABLE 15

| | Cyclodextrin addition level | Plasma level (μg/ml) | | | | | AUC (0–4 hr.) |
|---|---|---|---|---|---|---|---|
| | | 0.5 hr. | 1 hr. | 2 hr. | 3 hr. | 4 hr. | |
| Control | — | 1.76 | 2.21 | 3.00 | 3.49 | 2.54 | 10.32 |
| This invention | 10% (w/w) α-cyclodextrin | 3.84 | 5.32 | 7.37 | 6.26 | 5.32 | 22.20 |

EXAMPLE 1

In 8 ml of an isotonic phosphate buffer (pH 7.4) is dissolved 5000 U (about 200 mg) of porcine insulin. Then, 500 mg of α-cyclodextrin and 20 mg of chlorobutanol are added and thoroughly dissolved. The mixed solution is diluted with physiological saline to make 10 ml. This solution is put in a nasal spray applicator and administered at the dose level of 0.1 ml per dose.

EXAMPLE 2

In 40 ml of purified water are dissolved 200 mg of DN-1417, 200 mg of mannitol and 200 mg of β-cyclodextrin and the solution is freeze-dried. The dry product is then pulverized to give a powder about 20 to 250 microns in diameter. A 30 mg portion of the powder is filled into No. 4 (U.S. Pharmacopoeia XX) hard gelatin capsules. To administer the drug, this capsule is set on an exclusive dust applicator equipped with needles for piercing holes in the capsule and a rubber balloon for sending air into the capsule, both ends of the capsule are pierced, and the rubber balloon is compressed to dispense the powdery contents into the nasal cavity via the top hole.

EXAMPLE 3

In 16 ml of an isotonic buffer solution (pH 7.4) containing 0.12% of methylparaben and 0.01% of propylparaben are dissolved 1 g of α-cyclodextrin and 2 g of TAP-144, followed by addition of 200 mg of methylcellulose (Metolose 90SH 4000, Shin-Etsu Chemical Co., Ltd., Japan). The mixture is stirred well to give a homogeneous viscous liquid. This liquid is diluted with the buffer solution to take a total of 20 g. This liquid is put in a nasal spray applicator and administered into the nasal cavity.

EXAMPLE 4

In 16 ml of an isotonic buffer solution (pH 7.4) containing 0.03% of p-chloro-m-xylenol is dissolved 1 g of α-cyclodextrin and 2 g of TAP-144, followed by addition of 200 mg of methylcellulose (Metolose 90SH 4000, Shin-Etsu Chemical Co., Ltd., Japan). The mixture is stirred well to give a homogeneous viscous liquid. This liquid is diluted with the buffer solution to make a total of 20 g. This liquid is put in a nasal spray applicator and administered into the nasal cavity.

EXAMPLE 5

500 mg of natural LH-RH [the peptide of general formula (II) wherein $R_1$=His, $R_2$=Tyr, $R_3$=Gly, $R_4$=Leu, $R_5$=Gly—$NH_2$] and 1 g of α-cyclodextrin are placed in a mortar, in which they are mixed with a hot melt of 1 g lanolin. Then, Miglyol 812 [Dynamite Nobel] is gradually added under stirring to make 10 g of an oil suspension. This suspension is put in an applicator, equipped with a dropping pipet and directly administered into the nasal cavity at the dose level of 0.1 g/dose.

EXAMPLE 6

In 1 ml of physiological saline are dissolved 50 mg of α-cyclodextrin and 100000 U of α-interferon (human leukocyte interferon). This solution is put in a nasal applicator with a dropping pipet and administered into the nasal cavity at the level of 0.1 ml/dose.

EXAMPLE 7

In 10 ml of physiological saline are dissolved 2 mg of desmopressin and 1 g of γ-cyclodextrin followed by addition of 100 mg of methyl cellulose to give a viscous liquid. A 0.2 ml portion of this liquid is taken in an applicator and administered directly into the nasal cavity.

EXAMPLE 8

In physiological saline are dissolved 1 g of enkepharin and 3 g of α-cyclodextrin. This solution is put in a spray applicator and administered at the level of 0.2 ml per dose into the nasal cavity.

EXAMPLE 9

To 90 ml of warm water (about 60° to 80° C.), there is added 10 g of methylcellulose (Metolose 90SH 4000, Shin-Etsu Chemical Co.) and dispersed therein by adequate stirring. Then, 200 mg of TAP-144 and 10 g of α-cyclodextrin are together dissolved therein, 100 ml of cooled (about 4° to 10° C.) aqueous solution is added, the mixture is stirred well at room temperature until a homogeneous gel is obtained. The total quantity is adjusted to 200 g by addition of distilled water. The gel is defoamed by centrifugation and distributed into tubes, which are then sealed. A vaginal dosage form containing a single dose of 1 mg of TAP-144 is prepared by placing 1 g of this gel in an applicator.

EXAMPLE 10

Oxytocin (20,000 units) and 10 g of α-cyclodextrin are dissolved in an aqueous solution preliminarily prepared by dissolving 5.0 ml of acetic acid and 2.15 g of sodium acetate trihydrate in one liter of water and having a pH of 3.5 to 4.5, to make 200 ml of a solution. A pharmaceutical preparation for vaginal administration which contains 10 units of oxytocin per 0.1 ml (single dose) is prepared by filling a nozzle device-equipped applicator with the above solution.

EXAMPLE 11

In 200 ml of water, there are dissolved and dispersed 20 g of lactose and 20,000 units (about 800 mg) of porcine insulin, followed by lyophilization. Thereafter, the lyophilizate is ground and stirred well. To a 10.4 g portion of the lyophilizate, there is added a new 61.35 g portion of lactose, and the mixture is stirred well. Further, 10 g of α-cyclodextrin and 10 g of corn starch are added. After adequate mixing, 20 ml of a preliminarily prepared 10% hydroxypropylcellulose (HPC-L) in ethanol solution is added, the mixture is kneaded and granulated by sieving, and the granules are dried at room temperature under reduced pressure for 16 hours. To the granules, there are added 5 g of corn starch and 1.25 g of magnesium stearate. After adequate mixing, each 1 g portion of the mixture is compressed into a tablet. In this way, tablets for vaginal administration each containing 100 units of insulin are produced.

EXAMPLE 12

To a mixture of 125 mg of an LH-RH analog which is a polypeptide having the formula (Pyr)Glu-His-Trp-Ser-Tyr-D-Ala-Leu-Arg-Pro-NHCH$_2$-CH$_3$ [Biochemical and Biophysical Research Communications, vol. 60, No. 1, pages 406–413 (1974)] and 5 g of α-cyclodextrin, there is added 5 g of lanolin preliminarily melted by warming. After sufficient milling and mixing, 89.9 g of an oleaginous base (Witepsol) melted in advance at 50° C. was added portionwise with stirring. After adequate homogenization, a plastic container for making a vaginal suppository is filled with 0.8 g of the mixture and the whole is cooled to give a pharmaceutical preparation form for vaginal administration which contains 1 mg of the LH-RH analog per container.

EXAMPLE 13

α-Cyclodextrin (1 g) and 50,000,000 units of α-interferon (human leukocyte-derived interferon) are dissolved in a 0.2% aqueous carboxymethylcellulose solution to make 10 ml. A pharmaceutical preparation for vaginal administration containing 1,000,000 units of α-interferon per 0.2 ml thereof, which is a single dose, is produced by filling a nozzle device-equipped spray with the solution.

EXAMPLE 14

α-Cyclodextrin (0.5 g), thyroid hormone-releasing hormone (TRH) tartrate (141.4 mg; 100 mg as TRH) and glycerin (180 ml) are dissolved in distilled water to make 10 ml. A paper tampon (φ10 mm×25 mm) fixed on a plastic inserter is soaked with 1 ml of the solution to give a pharmaceutical preparation for vaginal administration containing 10 mg of TRH.

EXAMPLE 15

α-Cyclodextrin (1 g), 50,000,000 units of γ-interferon and 400 mg of human serum albumin are dissolved in 10 ml of distilled water. Glass bottles are each filled with 2 ml of the solution and the contents are lyophilized. Immediately before use, the lyophilizate is dissolved in 2 ml of a diluent of distilled water and the bottle is mounted on the adapter of a nozzle device-equipped spray to give a pharmaceutical preparation for vaginal administration containing 1,000,000 units of γ-interferon per 0.2 ml thereof (single dose).

EXAMPLE 16

Witepsol W-35 (9.316 g, Dynamite Nobel), a base, is weighed, placed in a mortar and melted by warming at 40°–45° C., and 500 mg of α- or β-cyclodextrin is added thereto. The mixture is stirred with warming. Then, 183.6 mg of DN-1417 citrate (corresponding to 120 mg of DN-1417) is added. The resultant mixture is stirred well and poured into a 1 g suppository mold and cooled gradually to give ten 1 g rectal suppositories.

EXAMPLE 17

In a mortar, there is placed 9.316 g of a mixed base composed of 75 w/w percent of polyethylene glycol (PEG) 1000 and 25 w/w percent of PEG 4000. The base is melted with warming at 50°–60° C. α- or β-cyclodextrin and DN-1417 citrate are added thereto and the mixture is treated in the manner in Example 16 to give ten 1 g rectal suppositories.

EXAMPLE 18

To 50 ml of an aqueous solution containing 0.12% of methyl paraben and 0.01% (w/w) of propyl paraben preliminarily dissolved therein by heating to 80°–90° C. (hereinafter, such solution is referred to as solution A), there is added 5 g of methylcellulose (Metolose 90SH 4000, Shin-Etsu Chemical Co.), and the mixture is stirred to prepare a dispersion. Thereto is added 38 ml of solution A containing 1.414 g of TRH tartrate (corresponding to 1 g of TRH) and 5 g of α-cyclodextrin dissolved therein. The resultant mixture is cooled to 4° to 10° C. and stirred well to give a homogeneous gel. After adjusting the total amount to 100 g, 1 g portion each of the gel is poured into applicators for rectal administration. There are thus produced gel suppositories for rectal administration.

EXAMPLE 19

To 50 ml of an aqueous solution containing 0.03% of p-chloro-m-xylenol (hereinafter, such solution is referred to as solution A), there is added 5 g of methylcellulose (Metolose 90SH 4000, Shin-Etsu Chemical Co.), and the mixture is stirred to prepare a dispersion. Thereto is added 38 ml of solution A containing 1.414 g of TRH tartrate (corresponding to 1 g of TRH) and 5 g of α-cyclodextrin dissolved therein. The resultant mixture is cooled to 4° to 10° C. and stirred well to give a homogeneous gel. After adjusting the total amount to 100 g, 1 g portion each of the gel is poured into applicators for rectal administration. There are thus produced gel suppositories for rectal administration.

EXAMPLE 20

Witepsol W-35 (a base, 9.388 g) is weighed, placed in a mortar and melted by warming at 40°–45° C., and 500 mg of α- or β-cyclodextrin is added thereto. The mixture is stirred with warming. Then, 112.4 mg of TAP-144 acetate (corresponding to 100 mg of TAP-144) is added. The resultant mixture is stirred well, poured into a 1 g suppository mold and cooled gradually to give ten 1 g rectal suppositories.

EXAMPLE 21

Porcine insulin (500 U, about 20 mg) is dissolved in 8 ml of an isotonic phosphate buffer (pH 7.4), and further 500 mg of α-, β- or γ-cyclodextrin and 20 mg of chlorobutanol are added. The mixture is stirred well and made up to 10 ml by addition of physiological saline, and 1 ml portions of the resulting solution are distributed into an inserter for rectal administration to give liquid dosage units for rectal administration.

EXAMPLE 22

Witepsol W-35 (a base, 9.25 g) is weighed, placed in a mortar and melted by warming at 40° to 45° C., and 500 mg of α- or β-cyclodextrin is added thereto. The mixture is stirred with warming. Then, 250 mg of enkephalin is added, and the resultant mixture is stirred well, poured into a 1 g suppository mold and cooled gradually to give ten 1 g rectal suppositories.

EXAMPLE 23

In a mortar, 3 g of lanolin is melted with warming, 0 616 mg (100,000 U) of sodium heparin and 1 g of α-cyclodextrin are added thereto, the mixture is mixed well for homogenization, and Miglyol 812 (Dynamite Nobel) is added gradually with stirring to make the whole weight 10 g. No. 0 (U.S. Pharmacopoeia XX) hard capsules are filled with 500 mg each portions of the resultant oleaginous suspension to give 20 rectal capsules.

EXAMPLE 24

Witepsol W-35 (a base, 15.5 g) is weighed, placed in a mortar and melted by warming at 40° to 45° C., and 2 g of α- or β-cyclodextrin is added thereto. The mixture is warmed and stirred. Then, 2.5 g of citicoline is added. The resultant mixture is stirred well, poured into a 2 g suppository mold and cooled gradually to give ten 2 g rectal suppositories.

EXAMPLE 25

In a mortar, 3 g of lanolin is melted with warming, 2 g of finely pulverized crystalline 5-FU and 1 g of α-cyclodextrin are added, the mixture is mixed well for homogenization, and Miglyol 812 (Dynamite Nobel) is added gradually with stirring to make the whole weight 10 g. No. 0 hard capsules are filled with 500 mg portions of the resultant oleaginous suspension to give 20 rectal capsules each containing 100 mg of 5-FU.

EXAMPLE 26

Witepsol W-35 (a base, 7 g) is weighed, placed in a mortar and melted by warming at 40° to 45° C., and 1.0 g of α- or β-cyclodextrin is added thereto. The mixture is stirred with warming. Then, 12 g of kanamycin sulfate [corresponding to 10 g (potency) of kanamycin] is added. The resultant mixture is stirred well, poured into a 2 g suppository mold and cooled gradually to give ten rectal suppositories.

EXAMPLE 27

Witepsol W-35 (a base, 7.885 g) is weighed, placed in a mortar and melted by warming at 40° to 45° C., and 1.000 g of α- or β-cyclodextrin is added thereto. The mixture is stirred with warming. Then, 11.115 g of sodium sulbenicillin [corresponding to 10 g (potency) of sulbenicillin] is added. The resultant mixture is stirred well, poured into a 2 g suppository mold and cooled gradually to give ten 2 g rectal suppositories.

EXAMPLE 28

Witepsol H-15 (61.5 g) is melted by warming, and 10 g of α-cyclodextrin and 28.5 g of finely pulverized cefotiam hydrochloride [corresponding to 25 g (potency) of cefotiam] are added thereto. After homogenization, the mixture is poured into a 2 g suppository mold and cooled gradually to give fifty 2 g rectal suppositories.

What we claim is:

1. A method for administering a pharmaceutical composition, which comprises administering a pharmaceutical composition containing a physical mixture of a hydrophilic, physiologically active polypeptide, which is poorly adsorbable through the gastrointestinal tract, and cyclodextrin through the rectum.

2. A method as claimed in claim 1, wherein the cyclodextrin is α-cyclodextrin.

3. A method as claimed in claim 1, wherein the pharmaceutical composition is a uniform mixture in dosage form.

4. A method as claimed in claim 1, wherein the physiologically active polypeptide is selected from the group consisting of L-pyroglutamyl-L-histidyl-L-prolinamide, its salts, a polypeptide represent by the formula:

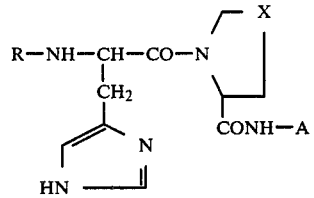

wherein A stands for hydrogen, alkyl, aralkyl, alkoxyalkyl, hydroxyalkyl or alkoxy, R stands for

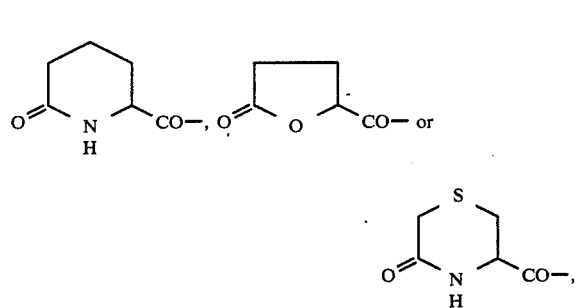

X stands for $-CH_2-$, $-CH_2CH_2-$ or $-S-$, R and each of the other constituent amino acid residues may have an L- or D-configuration or be racemic, and its salts.

5. A method as claimed in claim 1, wherein the physiologically active polypeptide is selected from the group consisting of luteinizing hormone-releasing hormone (LH-RH) and a peptide which has LH-RH activity and has the formula:

(Pyr)Glu-R$_1$-Trp-Ser-R$_2$-R$_3$-R$_4$-Arg-Pro-R$_5$ wherein R$_1$ stands for His, Tyr, Trp or p-NH$_2$-Phe; R$_2$ stands for Tyr or Phe; R$_3$ stands for Gly or a D-amino acid residue; R$_4$ stands for Leu, Ile or Nle; R$_5$ stands for Gly-NH-R$_6$ (R$_6$ stands for H or a lower alkyl group which may optionally have a hydroxyl group) or NH-$R_6$ ($R_6$ is as defined above).

6. A method as claimed in claim 1, wherein the physiologically active polypeptide is selected from the group consisting of insulin, somatostatin, somatostatin derivatives, growth hormone, prolactin, adrenocorticotrophic hormone, melanocyte stimulating hormone, thyrotropin releasing hormone, its salts or its derivatives, thyroid stimulating hormone, luteinizing hormone, follicle stimulating hormone, vasopressin, vasopressin derivatives, oxytocin, carcitonin, parathyroid hormone, glucagon, gastrin, secretin, pancreozymin, cholecystokinin, angiotensin, human placental lactogen, human chorionic gonadotropin, enkephalin, enkephalin derivatives, endorphin, interferon ($\alpha$, $\beta$, $\gamma$), urokinase, kallikrein, thymopoietin, thymosin, motilin, dynorphin, bombesin, neutotensin, caerulein, bradykinin, substance P, kyotorophin, nerve growth factor, polymyxin B, colistin, gramicidin, bacitracin, bleomycin and neocarzinostatin.

* * * * *